United States Patent
Becq et al.

(10) Patent No.: US 7,897,610 B2
(45) Date of Patent: Mar. 1, 2011

(54) USE OF BENZO[C]QUINOLIZINIUM DERIVATIVES FOR THE TREATMENT OF DISEASES THAT ARE LINKED TO SMOOTH MUSCLE CELL CONSTRICTION

(75) Inventors: Frédéric Becq, Bonnes (FR); Renaud Robert, Poitiers (FR); Laurence Pignoux, Jardres (FR); Christian Rogier, Poitiers (FR); Yvette Mettey, Poitiers (FR); Jean Michel Vierfond, Maisons Alfort (FR); Michel Joffre, Poitiers (FR); Cécile Marivingt-Mounir, Poitiers (FR)

(73) Assignees: Centre National de la Recherche Scientifique, Paris (FR); Universite de Poitiers, Poitiers (FR)

( * ) Notice: Subject to any disclaimer, the term of this patent is extended or adjusted under 35 U.S.C. 154(b) by 930 days.

(21) Appl. No.: 10/516,839

(22) PCT Filed: Jun. 5, 2003

(86) PCT No.: PCT/FR03/01688

§ 371 (c)(1),
(2), (4) Date: Mar. 4, 2005

(87) PCT Pub. No.: WO03/104228

PCT Pub. Date: Dec. 18, 2003

(65) Prior Publication Data

US 2005/0176747 A1    Aug. 11, 2005

(30) Foreign Application Priority Data

Jun. 5, 2002    (FR) .................................. 02 06916

(51) Int. Cl.
*A61K 31/4375*    (2006.01)
*C07D 455/06*    (2006.01)
(52) U.S. Cl. ........................................ 514/294; 546/95
(58) Field of Classification Search ................ 514/294; 546/95, 94
See application file for complete search history.

(56) References Cited

U.S. PATENT DOCUMENTS 6,630,482 B1 *  10/2003  Becq et al. .................. 514/294

FOREIGN PATENT DOCUMENTS

WO           98/05642        2/1998

* cited by examiner

*Primary Examiner*—Charanjit S Aulakh
(74) *Attorney, Agent, or Firm*—Clark & Elbing LLP

(57) ABSTRACT

The invention relates to the use of benzo[c]quinolizinium derivatives for treating diseases that are linked to smooth muscle cell constriction, such as hypertension and asthma.

13 Claims, 9 Drawing Sheets

A.

B.

A.

B.

A.

B.

C.

D.

A.

B.

USE OF BENZO[C]QUINOLIZINIUM DERIVATIVES FOR THE TREATMENT OF DISEASES THAT ARE LINKED TO SMOOTH MUSCLE CELL CONSTRICTION

This application is a U.S. national stage application under 35 U.S.C. § 371 of the PCT/FR03/01688, filed Jun. 5, 2003, which claims priority from French application number 02/06916, filed Jun. 5, 2002.

A subject of the present invention is the use of benzo[c] quinolizinium derivatives in the treatment of pathologies linked to smooth muscle cell constriction phenomena, such as arterial hypertension, or asthma.

A number of molecular activators have been synthesized with a view to their possible use in the treatment of cystic fibrosis (Becq et al., 1999; WO 98/05642). From these chemical syntheses a series of substituted benzo[c]quinolizinium compounds (MPB) have appeared and, among these molecules, the compounds MPB-07 and MPB-91. In cells expressing the CFTR protein in an endogenous manner, it has been demonstrated, by iodide efflux and patch clamp techniques, that MPB-07 and MPB-91 are activators of this ion channel (Becq et al., 1999, Derand et al., 2001). The inventors have shown that these two molecules modify the localization of delF508-CFTR in the pulmonary cells of patients homozygotic for this mutation, and that activation of the delF508 channel is restored after treatment (Dormer et al., 2001). The action mechanism has not been established but these two molecules do not affect the ATPase activity of the two NBF sites (Derand et al., 2001), nor the level of intracellular cAMP nor the phosphatase and kinase activities of the principal enzymes involved in the regulation of CFTR (Becq et al., 1999, Derand et al., 2001).

The present invention follows from the demonstration by the inventors of the effects of MPB-07 and MPB-91 on vascular reactivity. The inventors used rat aorta, an organ having the property of contracting (vasoconstriction) or relaxing (vasorelaxation) under the action of different (endogenous or exogenous) molecular or mechanical agents.

Thus the inventors have demonstrated that the benzo[c] quinoliziniums described hereafter within the scope of the present invention, such as MPB-07 and the MPB-91, are molecules capable of modulating the vascular tonus in humans and in rats by acting on the activity of the smooth muscle cells. Moreover, the inventors have demonstrated that CFTR is expressed and functional in the smooth muscle. These results demonstrate that a molecule which proves to be a CFTR activator can act as a potential vasorelaxant and bronchodilator.

Therefore, the present invention aims to provide new medicaments intended for the treatment of pathologies linked to a constriction of smooth muscle cells in tissues such as the pathologies linked to vasoconstriction phenomena within the scope of vascular disorders, in particular arterial hypertension, or the pathologies linked to bronchoconstriction phenomena within the scope of respiratory disorders, in particular asthma.

A subject of the present invention is the use of compounds activating the CFTR channel, such as the benzo[c]quinoliziniums, for the preparation of medicaments intended for the treatment of pathologies linked to a constriction of the smooth muscle cells in the tissues such as the pathologies linked to the phenomena of vasoconstriction within the scope of vascular disorders, in particular the arterial hypertension, or the pathologies linked to the phenomena of bronchoconstriction within the scope of respiratory disorders, in particular asthma.

A more particular subject of the present invention is the use of derivatives of the following general formula (I):

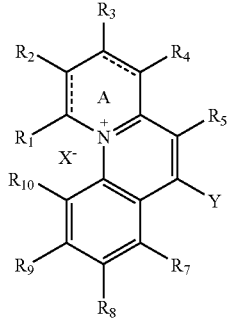

in which:
the heterocycle A is aromatic or non-aromatic, it being understood that in this latter case the nitrogen atom of this heterocycle is linked by a double bond to the carbon in position 4a, $R_1$, $R_2$, $R_3$, $R_4$, $R_5$, $R_7$, $R_8$, $R_9$ and $R_{10}$, represent, independently of one another:
  a hydrogen atom, or
  a halogen atom, in particular a chlorine, bromine, or fluorine atom, or
  an alkyl, alkoxy, carbonyl, oxycarbonyl or ester group, linear or branched, with approximately 1 to approximately 10 carbon atoms, these groups being if appropriate substituted, in particular by a halogen, and/or by a hydroxyl, and/or by a (primary, secondary or tertiary) amine, and/or by an aromatic and/or aliphatic ring, with approximately 5 to approximately 10 carbon atoms in the ring, these rings being themselves, if appropriate, substituted in particular by a halogen, and/or by a hydroxyl, and/or by a (primary, secondary or tertiary) amine, and/or by an alkyl, alkoxy, carbonyl, oxycarbonyl or ester group, these groups being as defined above, or
  an aromatic or aliphatic ring, with approximately 5 to approximately 10 carbon atoms in the ring, this ring being itself, if appropriate, substituted in particular by a halogen, and/or by a hydroxyl, and/or by a (primary, secondary or tertiary) amine, and/or by an alkyl, alkoxy, carbonyl, oxycarbonyl or ester group, these groups being as defined above, or
  an —$OR_a$ group, $R_a$ representing a hydrogen atom, or an alkyl, carbonyl, oxycarbonyl or ester group, linear or branched, these groups being as defined above, or an aromatic or aliphatic ring, these rings being as defined above, or
  an —$NR_bR_c$ group, $R_b$ and $R_c$, independently of one another, representing a hydrogen atom, or an alkyl, alkoxy, carbonyl, oxycarbonyl or ester group, linear or branched, these groups being as defined above, or an aromatic or aliphatic ring, these rings being as defined above, or
  when $R_1$ and $R_2$, and/or $R_3$ and $R_4$, and/or $R_4$ and $R_5$, and/or $R_7$ and $R_8$, and/or $R_8$ and $R_9$, and/or $R_9$ and $R_{10}$, do not represent the different atoms or groups or rings mentioned above, then $R_1$ in combination with $R_2$, and/or $R_2$ in combination with $R_3$, and/or $R_3$ in combination with $R_4$, and/or $R_4$ in combination with $R_5$, and/or $R_7$ in combination with $R_8$, and/or $R_8$ in combination with $R_9$, and/or $R_9$ in combination with $R_{10}$, respectively form with $C_1$ and $C_2$, or with $C_2$ and $C_3$, or with $C_3$ and $C_4$, or with $C_4$, $C_{4a}$ and $C_5$, or with $C_7$ and $C_8$, or with $C_8$ and $C_9$, or with $C_9$ and $C_{10}$, an aromatic or aliphatic ring with 5 to 10 carbon atoms, this ring being if appropriate substituted, in particular by a halogen, and/or by an alkyl, alkoxy, carbonyl, oxycarbonyl, or ester group, and/or by an aromatic or aliphatic ring, these groups or rings being as defined above, or when $R_3$ and $R_4$ do not represent the different atoms or groups or rings mentioned above, then $R_3$ in combination with $R_4$ forms an indole group of formula

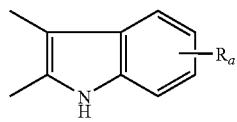

in which $R_a$ is as defined above,

Y represents:
- an —$OR_d$ group, $R_d$ representing a hydrogen atom, or an alkyl, carbonyl, oxycarbonyl or ester group, linear or branched, these groups being as defined above, or an aromatic or aliphatic ring, these rings being as defined above, or
- an —$NR_eR_f$ group, $R_e$ and $R_f$ independently of one another, representing a hydrogen atom, or an alkyl, alkoxy, carbonyl, oxycarbonyl or ester group, linear or branched, these groups being as defined above, or an aromatic or aliphatic ring, these rings being as defined above,
- or an SH group, it being understood that when $R_d$, or at least one of $R_e$ or $R_f$, do not represent one of the different atoms or groups or rings mentioned above, then $R_d$, or at least one of $R_e$ or $R_f$, in combination with $R_5$, or in combination with $R_7$, respectively form with $C_5$ and $C_6$, or with $C_6$, $C_{6a}$ and $C_7$, an aromatic or aliphatic heterocycle with 5 to 10 carbon atoms, if appropriate substituted, in particular by a halogen, and/or by an alkyl, alkoxy, carbonyl, oxycarbonyl or ester group, and/or by an aromatic or aliphatic ring, these groups or rings being as defined above, X represents an atom in anionic form, such as a halogen atom, in particular a bromine or chlorine atom, or a group of atoms in anionic form, such as a perchlorate, and the nitrogen of the heterocycle A of formula (I) is in quaternary form and is linked on the one hand by a covalent bond to the carbon in position 11, and, on the other hand, by ionic bond to X defined above, it being understood that when $R_1$ and $R_{10}$ do not represent one of the different atoms or groups or rings mentioned above, then $R_1$ in combination with $R_{10}$ forms with $C_1$, the nitrogen of the heterocycle A of formula (I), $C_{11}$, and $C_{10}$, an aromatic or aliphatic heterocycle with 5 to 10 carbon atoms, if appropriate substituted, in particular by a halogen, and/or by an alkyl, alkoxy, carbonyl, oxycarbonyl or ester group, and/or by an aromatic or aliphatic ring, these groups or rings being as defined above, for the preparation of medicaments intended for the treatment of pathologies linked to a constriction of smooth muscle cells in tissues such as the pathologies linked to vasoconstriction phenomena within the scope of vascular disorders, in particular arterial hypertension, or the pathologies linked to bronchoconstriction phenomena within the scope of respiratory disorders, in particular asthma.

A more particular subject of the invention is the use as described above, of the benzo[c]quinolizinium derivatives of the following formula (Ia):

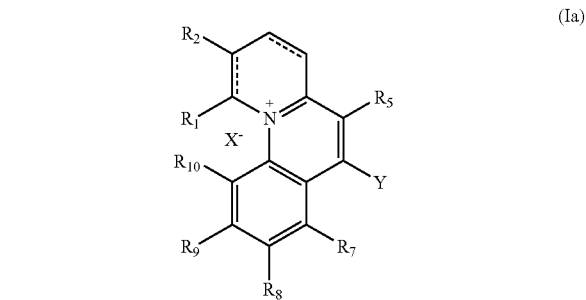

(Ia)

in which:
- $R_1$ and $R_2$ represent a hydrogen atom, or form in combination with $C_1$ and $C_2$ an aromatic ring with 6 carbon atoms,
- $R_5$ represents a hydrogen atom, or a linear or substituted alkyl group with 1 to 10 carbon atoms, in particular a butyl group, or an ester of formula COOR' in which R' represents a linear or substituted alkyl group with 1 to 10 carbon atoms, in particular an ethyl group,
- Y represents an —OH, —SH, —$NH_2$, or —$NHCOCH_3$ group,
- $R_7$, $R_8$, $R_9$ and $R_{10}$ represent a hydrogen atom, or at least one of $R_7$, $R_8$, $R_9$ or $R_{10}$, represents a halogen atom, in particular a chlorine, bromine or fluorine atom,
- X represents a halogen atom in anionic form, in particular a bromine Br$^-$, or chlorine Cl$^{-1}$ atom, or a group of atoms in anionic form.

A more particular subject of the invention is also benzo[c]quinolizinium derivatives of formula (Ia) as defined above, in which Y represents an —$NH_2$, or —$NHCOCH_3$ group.

Therefore, the invention also relates more particularly to the use as described above, of following benzo[c]quinolizinium derivatives of formula (Ia):

compound 13 (MPB-01)

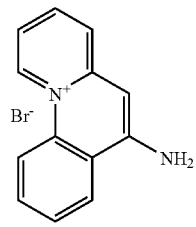

compound 11 (MPB-26)

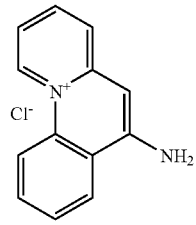

-continued compound 14 (MPB-02)
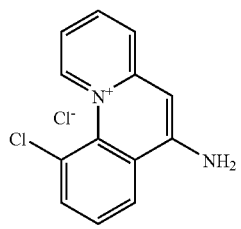

compound 15 (MPB-03)
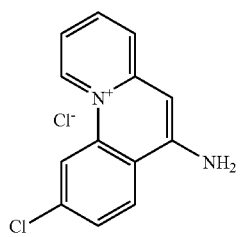

compound 16 (MPB-04)
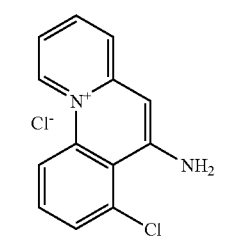

compound 17
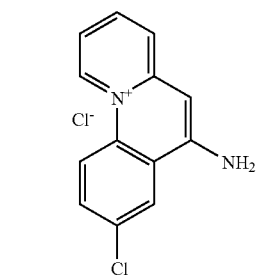

compound 22
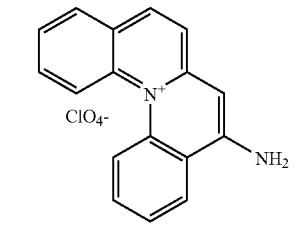

compound 23 (MPB-98)
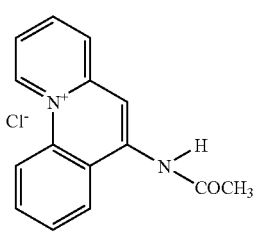

-continued compound 24
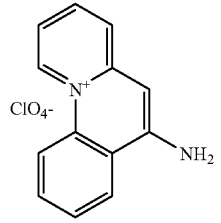

A more particular subject of the invention is also the use as described above, of benzo[c]quinolizinium derivatives of formula (Ia) as defined above, in which Y represents OH.

Therefore, the invention also relates more particularly to the use as described above, of following benzo[c]quinolizinium derivatives of formula (Ia):

compound 12 (MPB-05)
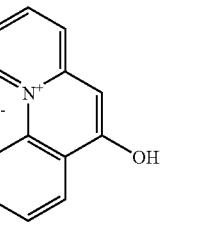

compound 18 (MPB-06)
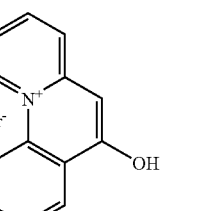

compound 19 (MPB-07)
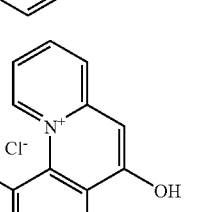

compound 20 (MPB-08)
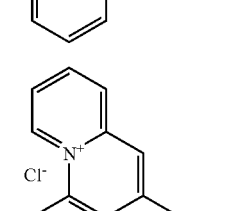

compound 21 (MPB-27)
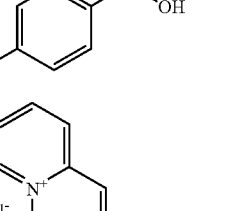

-continued compound 25 (MPB-30)
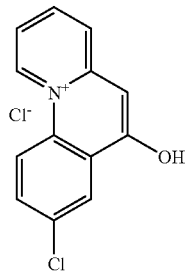

compound 26 (MPB-29)
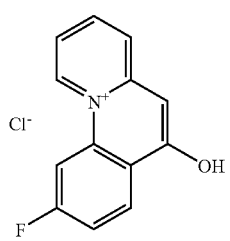

compound 27 (MPB-32)
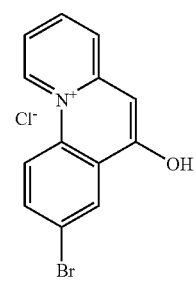

compound MPB-91
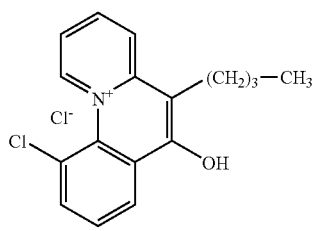

compound MPB 73
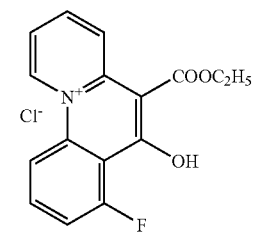

compound MPB 75
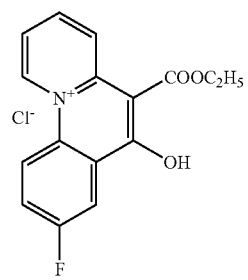

-continued compound MPB 86
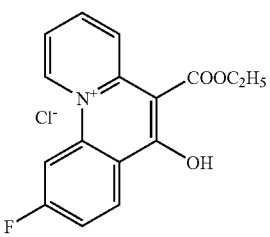

compound MPB 77
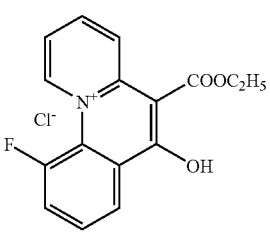

compound MPB 87
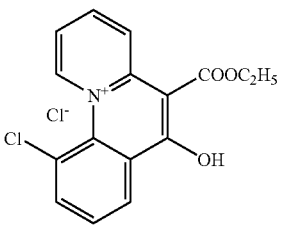

compound MPB 88
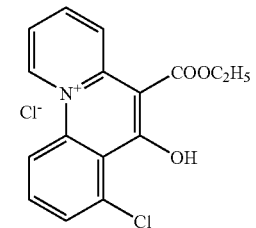

A more particular subject of the invention is also the use as described above, of benzo[c] quinolizinium derivatives of formula (Ia) as defined above, in which Y represents SH.

Therefore, the invention also relates more particularly to the use as described above, of following benzo[c]quinolizinium derivatives of formula (Ia):

compound MPB 102
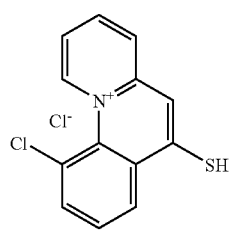

-continued

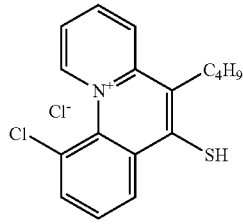

compound MPB 103

The invention also relates to the use as described above of derivatives of the following general formula (Ia-1):

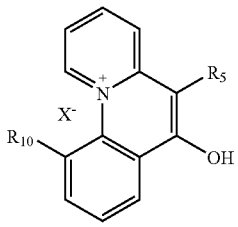

(Ia-1)

in which:

R$_5$ represents a hydrogen atom, or a linear or substituted alkyl group with 1 to 10 carbon atoms, in particular a butyl group, R$_{10}$ represents a halogen atom, in particular a chlorine, bromine or fluorine atom, X represents a halogen atom in anionic form, in particular a bromine Br$^-$ or chlorine Cl$^-$ atom, or a group of atoms in anionic form.

A more particular subject of the invention is the abovementioned use of the derivative of formula (Ia-1) defined above, and corresponding to compound MPB-07 of the following formula:

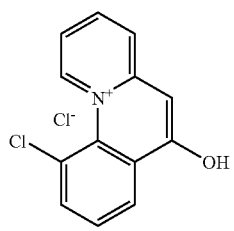

compound 19 (MPB-07)

The invention also relates more particularly to the abovementioned use of the derivative of formula (Ia-1) defined above, and corresponding to compound MPB-91 of the following formula:

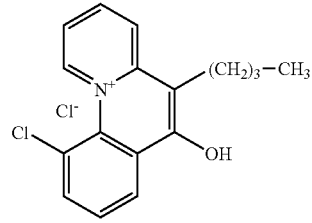

compound MPB-91

A subject of the invention is also the abovementioned use of derivatives of the following general formula (Ib):

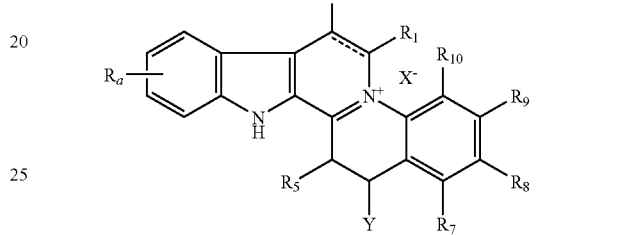

(Ib)

in which R$_a$, R$_1$, R$_2$, R$_5$, R$_7$, R$_8$, R$_9$, R$_{10}$, X and Y are as defined above, and in particular the compounds of formula (Ib) in which:

R$_a$ represents a hydrogen atom,

R$_1$ and R$_2$ represent a hydrogen atom, and there is no double bond between the two carbons carrying R$_1$ and R$_2$, R$_5$ represents a hydrogen atom, R$_7$, R$_8$, R$_9$ and R$_{10}$ represent a hydrogen atom, or one of R$_7$, R$_8$, R$_9$ or R$_{10}$ represents a halogen atom, in particular a chlorine, bromine or fluorine atom, Y represents NH$_2$, or OH, X represents a halogen atom, in particular a bromine, or chlorine, or fluorine atom.

A more particular subject of the invention is the abovementioned use of derivatives of the following formula (Ib-1):

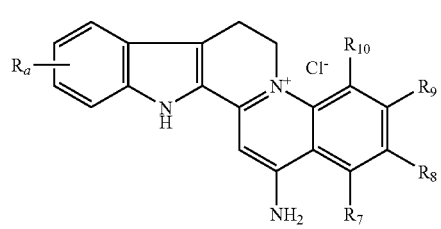

(Ib-1)

in which R$_a$, R$_7$, R$_8$, R$_9$, R$_{10}$, are as defined above, and more particularly the following compounds of formula (Ib-1):

compound G: R$_7$=Cl, R$_8$=R$_9$=R$_{10}$=H,
compound H: R$_7$=R$_8$=R$_9$=R$_{10}$=H,
compound I: R$_8$=Cl, R$_7$=R$_9$=R$_{10}$=H,
compound J: R$_9$=Cl, R$_7$=R$_8$=R$_{10}$=H,
compound K: R$_{10}$=Cl, R$_7$=R$_8$=R$_9$=H,
compound L: R$_9$=Br, R$_7$=R$_8$=R$_{10}$=H.

A subject of the invention is also the compounds of the abovementioned formula (I) in which $R_5$ represents an ester of formula COOR' in which R' represents a linear or substituted alkyl group with 1 to 10 carbon atoms, in particular an ethyl group.

A more particular subject of the invention is the compounds of the abovementioned formula (Ia) in which:

$R_1$ and $R_2$ represents hydrogen atom, or form in combination with $C_1$ and $C_2$ an aromatic ring with 6 carbon atoms, $R_5$ represents an ester of formula COOR' in which R' represents a linear or substituted alkyl group with 1 to 10 carbon atoms, in particular an ethyl group, Y represents an —OH, —SH, —$NH_2$, or —$NHCOCH_3$ group, $R_7$, $R_8$, $R_9$ and $R_{10}$ represent a hydrogen atom, or at least one of $R_7$, $R_8$, $R_9$ or $R_{10}$ represents a halogen atom, in particular a chlorine, bromine or fluorine atom, X represents a halogen atom in anionic form, in particular a bromine $Br^-$, or chlorine $Cl^-$ atom, or a group of atoms in anionic form.

A more particular subject of the invention is also the compounds of the abovementioned formula (Ia) in which $R_5$ represents an ester of formula COOR' in which R' represents a linear or substituted alkyl group with 1 to 10 carbon atoms, in particular an ethyl group, and Y represents an —OH group.

Therefore, the invention relates more particularly to the compounds of the abovementioned formula (Ia), and corresponding to the following formulae:

compound MPB 73 compound MPB 75 compound MPB 86 compound MPB 77 compound MPB 87 compound MPB 88

A subject of the invention is also the compounds of the abovementioned formula (I) in which Y represents SH.

A more particular subject of the invention is the compounds of the abovementioned formula (Ia) in which:

$R_1$ and $R_2$ represent a hydrogen atom, or form in combination with $C_1$ and $C_2$ an aromatic ring with 6 carbon atoms, $R_5$ represents a hydrogen atom, or a linear or substituted alkyl group with 1 to 10 carbon atoms, in particular a butyl group, Y represents an —SH group, $R_7$, $R_8$, $R_9$ and $R_{10}$ represent a hydrogen atom, or at least one of $R_7$, $R_8$, $R_9$ or $R_{10}$ represents a halogen atom, in particular a chlorine, bromine or fluorine atom, X represents a halogen atom in anionic form, in particular a bromine $Br^-$, or chlorine $Cl^-$ atom, or a group of atoms in anionic form.

Therefore, the invention relates more particularly to the compounds of the abovementioned formula (Ia), and corresponding to the following formulae:

compound MPB 102

-continued compound MPB 103

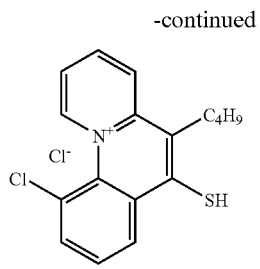

A subject of the invention is also any pharmaceutical composition comprising, as active ingredient(s), at least one of the compounds of general formula (I) described above, and more particularly at least one of the compounds of the abovementioned formula (Ia) in which $R_5$ represents an ester of formula COOR' in which R' represents a linear or substituted alkyl group with 1 to 10 carbon atoms, in particular an ethyl group, and/or Y represents SH, in combination with a physiologically acceptable vehicle.

Therefore, a more particular subject of the invention is the abovementioned pharmaceutical compositions comprising at least compound MPB 73, MPB 75, MPB 86, MPB 77, MPB 87, MPB 88, MPB 102, or MPB 103, in combination with a physiologically acceptable vehicle.

Preferred pharmaceutical compositions used within the scope of the present invention are those comprising compound 19 (also designated MPB-07), or compound MPB-91, if appropriate in combination with one (or more) other compound(s) of the invention described above.

Advantageously the pharmaceutical compositions according to the invention are presented in a form which can be administered by oral route, in particular in the form of tablets, or gelatin capsules, or in a form which can be administered by parenteral route, in particular in the form of injectable preparations by intravenous, intramuscular, or sub-cutaneous route, or also via the airways, in particular by pulmonary route in the form of aerosols.

Advantageously also, the pharmaceutical compositions according to the invention, are characterized in that the quantities of active ingredient(s) are such that the daily dose of active ingredient(s) is approximately 0.1 mg/kg to 5 mg/kg, in particular approximately 3 mg/kg, in one or more doses.

As regards the synthesis of the compounds of formula (I) of the invention, the latter is described in full detail in the international Application WO 98/05642, as well as in the article by Becq et al., 1999, and by Derand et al., 2001.

The invention is further illustrated by the following detailed description of the synthesis of novel compounds of the invention, and the study of the compounds of the invention within the scope of vasodilatation.

I) Preparation of Compounds MBP 73, MPB 75, MPB 86, MPB 77, MPB 87, and MPB 88

A solution of 0.025 mole BuLi is added dropwise with a syringe to a solution of 4.03 g (0.025 mole) of 1,1,1,3,3,3-hexamethyldisilazane in 10 mL of THF (at −5° C.) in a three-necked flask equipped with a nitrogen supply and dropping funnel. The mixture is stirred at −5° C. for 30 minutes. A solution of 3.30 g (0.02 mole) of ethyl 2-pyridylacetate in 25 mL of THF is added dropwise over 2 hours. Then a solution of 0.018 mole of difluorinated (MBP 73, MPB 75, MPB 86, MPB 77), or dichlorinated (MPB 87, and MPB 88) benzoyl chloride in 10 mL of THF is added over 1 hour. The mixture is maintained under stirring at −5° C. for 1 hour and at laboratory temperature for 2 hours. After hydrolysis with 20 mL of water, the solvent is eliminated under reduced pressure.

The compounds cyclized during the evaporation of the reaction solvent are purified by silica gel column chromatography, elution by ethyl acetate. 0.0003 mole of previously obtained compounds are put into solution in a mixture of anhydrous methylene chloride (5 mL) and anhydrous ether (50 mL), the hydrochloric alcohol is added until precipitation is finished. The precipitate is filtered on Büchner then rinsed with anhydrous ether.

5-carboxyethyl-6-hydroxy-10-fluorobenzo[c]quinolizinium chloride MPB 77

Powdery cream product Yield: 50%
Melting point: 134° C.
Ultimate analysis calculated for $C_{16}H_{13}NO_3ClF$, 0.5 $H_2O$: C, 58.10; H, 4.26; N, 4.23. Found C, 58.62; H, 3.88; N, 4.16.
NMR $^1H$ (DMSOd$_6$) δ ppm, signal, n protons, attribution: 8.9, peak poorly resolved, 1H, $H_1$; 8.2 to 6.9, multiplet, 6H, aromatic protons; 6.3, 1H, singlet, OH; 4.3, quadruplet (J=7 Hz), 2H, $CH_2$; 1.3, triplet (J=7 Hz), 3H, $CH_3$. IR (KBr) ν cm$^{-1}$, attribution: 3420 OH, 3171 3080 C=C—H, 2973 C—C—H, 1718 C=O, 1628, 1560, 1520, 1506, 1458, 1312, 1284, 1267, 1193, 1175, 1026, 824, 774.

5-carboxyethyl-6-hydroxy-9-fluorobenzo[c]quinolizinium chloride MPB 86

Powdery yellow product Yield: 63%
Melting point: 154° C.
Ultimate analysis calculated for $C_{16}H_{13}NO_3ClF$: C, 59.73; H, 4.07; N, 4.35. Found C, 59.58 ; H, 4.10; N, 4.28.
NMR $^1H$ (DMSOd$_6$) δ ppm, signal, n protons, attribution: 9.2, doublet (J=8 Hz), 1H, $H_1$; 8.7 to 7.1, multiplet, 6H, aromatic protons; 5.7, exchangeable singlet, 1H, OH; 4.3, quadruplet (J=7 Hz), 2H, $CH_2$; 1.3, triplet (J=7 Hz), 3H, $CH_3$. IR (KBr) ν cm$^1$, attribution: 3454 OH, 3104 3047 3016 C=C—H, 2960 C—C—H, 1727 C=O, 1609, 1535, 1471, 1435, 1323, 1308, 1259, 1215, 1108, 1017, 831, 764.

5-carboxyethyl-6-hydroxy-8-fluorobenzo[c]quinolizinium chloride MPB 75

Powdery yellow product Yield: 28%
Melting point: 168° C.
Ultimate analysis calculated for $C_{16}H_{13}NO_3ClF$: C, 59.73; H, 4.07; N, 4.35.
Found C, 59.54 ; H, 4.07; N, 4.24.
NMR $^1H$ (DMSOd$_6$) δ ppm, signal, n protons, attribution: 9.4, doublet (J=9 Hz), 1H, $H_1$; 8.9 to 8.7, multiplet, 1H, aromatic proton; 8.2 to 7.0, multiplet, 5H, aromatic protons; 6.0, exchangeable singlet, 1H, OH; 4.3, quadruplet (J=8 Hz), 2H, $CH_2$; 1.3, triplet (J=8 Hz), 3H, $CH_3$. IR (KBr) ν cm$^{-1}$, attribution: 3500 OH, 3157 3049 C=C—H, 2960 C—C—H, 1670, 1626, 1590, 1532, 1503, 1457, 1323, 1259, 1209, 1006, 885, 792.

5-carboxyethyl-6-hydroxy-7-fluorobenzo[c]quinolizinium chloride MPB 73

Powder cream product Yield: 27%
Melting point: 173° C.
Ultimate analysis calculated for $C_{16}H_{13}NO_3ClF$, 0.5 $H_2O$: C, 58.10; H, 4.26; N, 4.23. Found C, 57.99; H, 4.12; N, 4.97.
NMR $^1H$ (DMSOd$_6$) δ ppm, signal, n protons, attribution: 9.0, doublet (J=8 Hz), 1H, $H_1$; 8.4 to 6.8, multiplet, 7H, aromatic protons+OH; 4.2, quadruplet (J=7 Hz), 2H, $CH_2$; 1.3, triplet (J=7 Hz), 3H, $CH_3$. IR (KBr) v $cm^{-1}$, attribution: 3420 OH, 3160 3101 3046 C=C—H, 2984 C—C—H, 1720 C=O, 1646, 1617, 1601, 1501, 1446, 1409, 1347, 1323, 1274, 1227, 1134, 1011, 814, 779.

5-n-Butyl-10-chloro-6-hydroxybenzo[c]quinolizinium chloride (MPB-91)

2-pentylpyridine was obtained in a first phase by condensation of 2-picolyllithium with 1-bromobutane at −40° C., and purified by silica gel column chromatography using dichloromethane as eluent. Then, 4.48 g (0.03 mol) of 2-pentylpyridine in solution in THF (30 mL) was treated at 0° C. with lithium diisopropylamide (0.033 mol), cooled down to −40° C., and 3.08 g (0.015 mol) of methyl 2,3-dichlorobenzoate in THF (15 mL) was added. The mixture was stirred for 1 hour at −40° C. and hydrolyzed at 20° C. with 10 mL of water. The organic phase was dried over $Na_2SO_4$, concentrated under vacuum and purified by column chromatography with petroleum ether and ethyl acetate as eluent. The pure product was heated to 200° C. for 1 hour. The residue was subjected to chromatography on florisil with dichloromethane in order to obtain the cyclic ketone. The latter was solubilized in anhydrous ether and a solution of HCl/ethanol was added dropwise. Powdery cream product; melting point=160° C., yield: 15%. Anal. $C_{17}H_{17}N_1O_1Cl_2$: C, 63.37; H, 5.32; N, 4.35; Found: C, 63.36; H, 5.27; N, 4.32. IR (KBr): 3439, 3121, 2951, 2923, 2895, 2863, 2496, 2344, 1629, 1589, 1502, 1488, 1457, 1400. $^1$H NMR ($Me_2SO$-$d_6$): σ 9.25 (δ, J=7 Hz, 1 H, H1), 8.5 (d, J=7 Hz, 1 H), 8.1-6.9 (m, 5H+OH), 2.9 (t, J=4 Hz, 2H, $CH_2$), 1.5-1.3 (m, 4H, 2 $CH_2$), 0.9 (t, 3 H, $CH_3$). Mass spectrum (ESI): 286 (M-HCl).

II) Pharmacological Effects of the Compounds of the Invention

The pharmacological effects of the compounds of the benzo[c]quinolizinium family, CFTR activators: 6-hydroxy-10-chlorobenzo[c]quinolizinium chloride (reference name: MPB-07) and 5-butyl-6-hydroxy-10-chlorobenzo[c]quinolizinium chloride (reference name: MPB-91), were studied on aorta rings isolated from rats and from human mammary arteries.

The results show the following facts (1) MPB-91 ($EC_{50}$=21 μM) and MPB-07 ($EC_{50}$=134 μM) have a reversible and slow dose-dependent vasorelaxant effect, on both preparations.

(2) These compounds activate anionic transport in smooth muscle cells. The activation profile of this transport (MPB-91, MPB-07) is similar to that encountered in epithelial cells expressing CFTR protein.

Vasodilator Effects of the Compounds of the Benzo[c]quinolizinium Family.

Materials and Methods

A. Biological Material

Sampling and Dissection of Rat's Aorta

The experiments are carried out on the thoracic aorta of male rats of Wistar strain weighing 200 to 250 g, 7 to 8 weeks of age. The rat is stunned then placed in the supine position. After thoracotomy, the segment of the aorta comprised between the diaphragm and the right aortic arch is excised. The portion of aorta is immediately placed in a buffered physiological solution of modified Krebs type. The aorta is sectioned into 5 mm rings.

Abrasion of the Endothelium

For certain preparations, the endothelium is removed mechanically using a needle surrounded by a wire which is turned in the aorta ring. This process does not damage smooth muscle cells.

B. Isolated Organs Technique

Mounting in the Isolated Organ Chamber

The aorta rings, after dissection, are suspended between two hooks one of which is fixed and the other is mobile. This mounting is placed in a chamber of Plexiglas (Emka Technologies), thermostatically-controlled at 37° C., containing 5 ml of physiological solution oxygenated by a gas mixture (95% $O_2$-5% $CO_2$). The thermostatically-controlled enclosure is supplied by a water bath. The mobile hook is suspended with a sensor connected to the interface (electromechanical transducer). This interface is connected on the one hand to an amplifier (amplification of the signal) and on the other hand to a computer (display and analysis of the signal). The IOX 1.565 program enables the processing and display of the signals on the computer screen. The Data Analyst and Prism 3.0 programs allow analysis of the results.

Operating Principle

The isometric force developed by the arterial preparations is converted into a potential difference which is amplified then transcribed into a signal which is displayed on a computer screen.

Methodology

After mounting the aorta rings in the experimental device, these are stretched at a basal tension of 2.5 g. This tension corresponds to the optimum point of their tension/length relationship. Waiting for a stable state in the reference physiological medium is carried out over a period of approximately 1 hour with washing every 20 minutes. Following this equilibration period, the different experiments are carried out.

Test of the Endothelial Function

In order to be free of the relaxation/contraction mechanisms due to the endothelium, certain preparations are made devoid of the latter by mechanical destruction. In order to ensure effective destruction of the endothelium, a cholinergic test (ACh $10^{-4}$ M) is carried out at the end of the first period of equilibration, on preparations pre-contracted by a hyperpotassium solution (80 mM of KCl). This test is considered valid if the addition of Ach does not cause relaxation and that the preparation remains in the contracted state.

Following this test, the preparations are subjected to several successive washings in order to re-establish a stable state. Once a stable state is reached, the different experiments can be carried out. The contractures due to the hyperpotassium solutions are obtained by the total replacement of the reference physiological solution by the hyperpotassium solution. The administration of the pharmacological substances is carried out in a cumulative fashion and directly in the isolated organ chambers whilst paying attention that the additional volume is not too high. The application of each new concentration only occurs after stabilization. In order to be aware of the reactivity state of the preparation at the end of manipulation, a hyperpotassium or noradrenergic test is carried out. If the preparation reacts in the direction of a contracture, the test is valid.

C. The Different Physiological Solutions and Pharmacological Substances Used

Physiological Solutions

The composition of the reference physiological solution is a solution of modified Krebs type: NaCl: 120 mM; KCl: 4.7 mM; $CaCl_2$: 2.5 mM; $MgCl_2$: 1.2 mM; $NaH_2PO_4$: 1.2 mM; $NaHCO_3$: 15 mM; Hepes: 10 mM; Glucose: 11 mM; pH=7.4. Hyperpotassium solutions containing different concentrations of KCl have been prepared according to the same principle. These solutions are used to provoke a contracture of the aorta ring by depolarisation of the smooth muscle cells. The hyperpotassium solution mainly used in the experiments contains 80 mM of KCl.

Pharmacological Substances

MPB-07 (6-hydroxy-10-chlorobenzo[c]quinolizinium chloride)

MPB-91 (5-butyl-6-hydroxy-10-chlorobenzo[c]quinolizinium chloride)

Arterenol (norepinephrine, SIGMA, USA)

ACh (acetylcholine, SIGMA, USA)

L-NAME (N.-nitro-L-arginine methyl ester, SIGMA, USA)

MPB-70 (10-chlorobenzo[c]quinolizine-6-one)

Verapamil (SIGMA, USA)

D. Iodide Efflux

The iodide efflux technique, perfected by Venglarick et al. (1990), allows measurement of the movement of ions and is described in detail in Derand et al. (2001).

Methodology

The aorta rings of equivalent size, are incubated in 1 ml of filling solution composed of physiological solution of modified Krebs type or hyperpotassium solution (80 mM KCl) supplemented with 1.5 µl/ml of Na $^{125}$I and 0.1 µl/ml of KI. After incubation for 1 hour 30 minutes at 37° C., 4 successive rinsings of two minutes are carried out in 1 ml of appropriate physiological solution (normal Krebs or hyperpotassium solution). An iodide efflux kinetics of the aorta rings is carried out for 12 min. After each minute, the content of each well is sampled and placed in hemolysis tubes, and radioactivity is counted with a gamma counter (Packard, Cobra II). At the $12^{th}$ minute, the aorta rings are solubilized in Sodium Dodecyl Sulphate (SDS 0.1%)+NaOH (0.1 M). This stage allows the recovery of the residual radioactivity by cell destruction.

Presentation of the Results

The total radioactivity of the cells is calculated by the addition of the counts per minute (cpm) of each collected fraction and of the cpm of the solubilized fraction (residual radioactivity). The curves are plotted expressing the efflux as a percentage of the cell content accumulated in the medium as a function of time. For example, the value attributed at time $t_n$, corresponds to: $100 \times (\Sigma$ cpm obtained from $t_0$ to $t_n$)/total radioactivity. The instantaneous discharge speed is presented according to the formula $Ln(^{125}It_1/^{125}It_2)/(t_1-t_2)$, where $t_1$ and $t_2$ are two successive times and $^{125}It_1$ and $^{125}It_2$ are the effluxes measured at time $t_1$ and $t_2$. In order to evaluate the effect of a substance, the activation ratio r=discharge speed after stimulation/discharge speed before stimulation is determined. The results (average±SEM) are compared using Student's statistical test for a paired value.

Results

A. Isolated Organs

1/Control Experiments

Hyperpotassium Contracture and Arterenol Contracture (FIG. 1A B)

After a state of stability of the aorta rings in normal Krebs-type solution, all of the solution is replaced by a hyperpotassium solution containing 80 mM of KCl. This solution has the effect of contracting the aorta rings by depolarization of the smooth muscle cells. FIG. 1A shows that the contracture obtained in hyperpotassium medium is stable over time. It is taken as a control (100% contracture) in the different experiments carried out. Contracture by arterenol ($10^{-4}$ M) is carried out by direct addition to the chamber containing the normal Krebs-type solution. The mechanism which leads to the contracture of the aorta is different. The arterenol binds to an alpha 1 type adrenergic receptor integrated to the membrane of the smooth muscle cells. This is the classic route via the DAG and the $IP_3$ which allows the contracture.

Validation of the Deendothelization Technique

In order to verify the presence or absence of the endothelium, the cholinergic test is used. After contracture of the aorta ring in hyperpotassium medium (80 mM of KCl), ACh ($10^{-4}$ M) is added to the chamber. The results show that the aorta rings without endothelium remain contracted whereas the aorta rings with endothelium relax (approximately 40% relaxation). In this study this test was validated.

Effects of Different Solvents, Solutions and Substances

Before commencing the experiments, different control tests with various substances were carried out in order to anticipate their possible effects on the preparations. The addition of water and DMSO (dimethylsulphoxide), the main solvents of the majority of substances injected into the preparations, have no effect on the aorta rings, whether the latter are in normal Krebs solution or in hyperpotassium solution.

Control of the pH

The normal Krebs or hyperpotassium solutions have a pH of 7.4. Over a 7-hour experiment, this pH shows no deviation, under both conditions. After addition of MPB-07 or other pharmacological substances used, the pH shows no deviation over time.

Deviation of the Contracture of the Aorta Rings Over Time

The aorta rings pre-contracted either by a hyperpotassium solution or by arterenol, show stable contracture over time, approximately one hour after the stable state of contracture is reached.

2/Effect of MPB-07 on Aorta Rings Pre-contracted in Hyperpotassium Solution

Aorta Rings with Endothelium (FIG. 2A; FIG. 3A)

MPB-07 causes a dose-dependent relaxation of the aorta rings with endothelium as shown by FIG. 2A. The results presented in FIG. 3A are expressed as a percentage of the maximum contracture achieved in hyperpotassium solution. FIG. 3A shows that on aorta rings with endothelium, MPB-07 has an $EC_{50}$=132.4±0.02 µM (n=14). Relaxation is effective from 80 µM (24±1.6% relaxation, n=14) and reaches 96±1.75% (n=14) for 500 µM.

Aorta Rings without Endothelium (FIG. 3B)

MPB-07 causes dose-dependent relaxation of the aorta rings without endothelium. This molecule therefore has an independent endothelium action. The results are presented as a percentage of the maximum contracture achieved in hyperpotassium solution. On the aorta rings without endothelium, FIG. 3B shows that the MPB-07 has an $EC_{50}$=92.90±0.02 µM (n=7). Relaxation is conclusive from 80 µM (37±5.6% relaxation, n=7) and reaches 99±1% (n=7) at 250 µM. In comparison with the previous result, MPB-07 seems more effective on the aorta rings without endothelium than on the aorta rings with endothelium, the two $EC_{50}$s are significantly different (Student's test, p<0.01). The absence of endothelium therefore plays a role in the relaxant effect caused by MPB-07.

Aorta Rings With Endothelium+L-NAME (FIG. 2B; FIG. 3C)

L-NAME was used in order to inhibit the regulation mechanisms of the endothelium on the smooth muscle cells and with the aim of mimicking an absence of the endothelium. This molecule is an NO (nitric oxide) synthase inhibitor present in endothelial cells. L-NAME ($10^{-4}$ M) is added to the hyperpotassium solution 30 minutes before the range of MPB-07. MPB-07 causes a dose-dependent relaxation of the aorta rings with endothelium treated with L-NAME as shown in FIG. 2B. The results (FIG. 3C) are presented as a percentage of the maximum contracture obtained in hyperpotassium solution after the addition of the L-NAME. The MPB-07 has an $EC_{50}=51.80\pm0.008$ µM (n=8). The relaxation becomes pronounced from 40 µM (33±6.15% relaxation, n=8) and reaches 98±1.3% for 160 µM. In comparison with the previous results, the presence of L-NAME potentializes the vasorelaxant effect of MPB-07.

Aorta Rings without Endothelium in the Presence of L-NAME (FIG. 3D)

The effect of MPB-07 was tested on aorta rings without endothelium and in the presence of L-NAME in order to block the regulation route by NO. In this situation, MPB-07 causes a dose-dependent relaxation of the aorta rings with an $EC_{50}=55.1\pm0.2$ µM (n=7). It should be noted that the curves "with endothelium+L-NAME" and "without endothelium+L-NAME" are comparable. FIGS. 5A and 5B show the statistical differences between the curve "with endothelium" and the curves "without endothelium" and "with endothelium+L-NAME".

3/Reversibility of the Effect of MPB-07 (FIG. 4A)

We have just shown that MPB-07 induced a vasorelaxation of the aorta rings pre-contracted in hyperpotassium solution. This effect is reversible as shown in FIG. 4A. In this experiment the addition of MPB-07 in a single dose (135 µM) causes a relaxation of the pre-contracted aorta rings with endothelium in hyperpotassium medium. After a stable state of relaxation, the rings are washed with normal physiological medium in order to return to the basal contracture state, then contracted again in hyperpotassium medium. The results (n=4) show a positive reactivity of the aorta rings, after a single dose of MPB-07, the latter recovering their initial hyperpotassium contracture. These results show the reversibility of the relaxing effect of MPB-07.

4/ Effect of MPB-07 on Aorta Rings Pre-contracted by Arterenol

FIG. 4B shows that the addition of MPB-07 (10 µM) causes a relaxation of the aorta rings with endothelium pre-contracted by arterenol ($10^{-4}$M). The results show 90±9% relaxation after 2 hours 30 minutes. Rapid contracture oscillations are observed. These transitory variations have an amplitude which increases as a function of time. The addition of verapamil ($Ca_L$ channel inhibitor, 200 µM) stops these variations.

5/ Comparison of the Effect of MPB-07 with the Effect of MPB-91 and MPB-70 (FIGS. 5C and 6)

MPB-07 and MPB-91 are CFTR activators. It appeared useful to us to compare their effects with MPB-70, an analogue inactive on CFTR of epithelial cells, the formula of which is the following

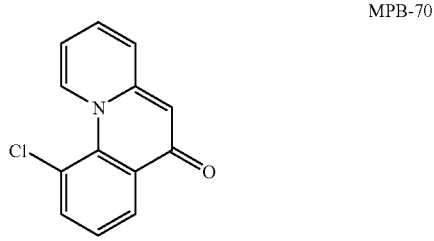

MPB-70

From 10 µM to 80 µM the effect of both molecules is similar, the results do not show any statistically significant difference. At 160 µM, MPB-70 relaxes the aorta rings (n=7) by 27% vs. 64% with MPB-07 (n=14): this difference is significant (***; p<0.001). At 250 µM, MPB-70 causes a 42% relaxation of the aorta rings whereas MPB-07 at this same concentration causes an 88% relaxation (statistically significant difference, p<0.001). At 500 µM, MPB-07 relaxes the aorta rings 100% whereas the percentage of relaxation by MPB-70 varies little (46%) and remains the same for higher concentrations. The comparison of the dose/response curves shown in FIG. 6 shows that MPB-91 ($EC_{50}=21$ µM) is more effective than MPB-07 ($EC_{50}=133$ µM).

6/ Conclusion

This study shows that:

MPB-07 and MPB-91 have a reversible and slow, dose-dependant vasorelaxant effect on pre-contracted aorta rings.

Inhibition of the NO-synthase route by L-NAME reinforces this pharmacological effect.

The order of effectiveness of the compounds is MPB-91>MPB-07>>MPB-70 on these preparations and follows that observed on human epithelial CFTR.

B. Iodide Effluxes

The iodide efflux technique was used to characterize the anionic transports and their method of stimulation by MPB-07. This technique makes it possible to trace an ionic transport in a cell charged beforehand with the corresponding radiotracer. We adapted this technique used routinely in the laboratory for the study on aorta rings.

We first studied the $^{125}I$ discharge kinetics of the smooth muscle cells of the aorta rings (devoid of endothelium) in the basal state, i.e. in the absence of stimulation. These experiments were carried out under two conditions: in normal physiological medium and in hyperpotassium medium. This study makes it possible to compare the results obtained after stimulation of the aorta rings. The results show that the iodide discharge occurs regularly as a function of time. The basal efflux corresponds to the passive diffusion of the radioactive charge outside the cells. These experiments show that the absence of discharge speed corresponds to the absence of anionic transport stimulation.

1/ Effect of MPB-07 on Iodide Effluxes, on Aorta Rings without Endothelium in Hyperpotassium Medium (80 mM KCl) (FIGS. 7A and 8A)

In the same experimental situation as that used in isolated organs the addition of MPB-07 causes an increase in the iodide efflux as shown in FIG. 7A. The discharge speed increases from 0.053±0.005 in the basal state to 0.076±0.008 (increase of 0.023) one minute after the addition of MPB-07, then to 0.099±0.013 (i.e. an increase of 0.046) 2 minutes after the addition of the molecule (results of n=8 experiments). These results show that MPB-07 activates anionic transport under these conditions. FIG. 8A shows the statistical differences between the discharge speed before and after stimulation by MPB-07.

2/ Effect of MPB-07 on Iodide Effluxes, on Aorta Rings with Endothelium Treated with L-NAME, in Hyperpotassium Medium (FIGS. 7B and 8B)

The addition of MPB-07 causes an increase in the efflux (FIG. 7B). In the presence of L-NAME ($10^{-4}$ M) this increase is higher than in the previous experiment. In fact, the discharge speed passes from 0.059 in the basal state to 0.103±0.017 (increase of 0.044) one minute after the addition of MPB-07, then to 0.110±0.015 (increase of 0.051) 2 minutes after the addition of MPB-07, to reach 0.119±0.011 (increase of 0.060) 3 minutes after the addition of the molecule (results of n=4 experiments). The increase in discharge speed is statistically significant compared with the basal value (FIG. 8B). These results show that the anionic transport activated by MPB-07 (250 µM) is potentialized by the presence of L-NAME. The NO synthase inhibition potentializes the activation of an anionic transport by MPB-07. This result backs up the results obtained in isolated organs.

3/ Effect of MPB-70 on Iodide Effluxes, on Aorta Rings without Endothelium, in Hyperpotassium Medium (FIGS. 7C and 8C)

MPB-70 is a molecule of the same family as MPB-07, but inactive on the CFTR channel. As in isolated organs, MPB-70 was tested in radiotracer efflux. On the aorta rings, the addition of MPB-70 causes no increase in the discharge speed. The discharge speed passes from 0.056±0.002 to 0.053±0.003 one minute after the addition of MPB-70. This speed only reaches 0.055±0.005, 2 minutes after the addition of the molecule.

4/ Effect of MPB-07 on Iodide Effluxes, on Aorta Rings without Endothelium in Normal Physiological Medium (FIGS. 7D and 8D).

Stimulation by MPB-07 leads to slight activation of the iodide efflux. This is expressed by an increase in the discharge speed which passes from 0.044±0.009 to 0.076±0.016 over n=3 experiments. Statistically this increase is not significant (ns) as shown in FIG. 8D.

5/ Conclusion

MPB-07 activates anionic transport in the smooth muscle cells, potentialized by L-NAME. The activation profile of this transport (MPB-07>>>MPB-70) is similar to that encountered in epithelial cells expressing human CFTR. Similar effects have been observed with compound MPB-91.

C. Demonstration of the Expression of CFTR Protein in the Smooth Muscle Cell of Rat and Mouse Aorta.

CFTR is detected at the level of its messenger RNA and at the level of protein in the smooth muscles. As negative control the inventors used musculus skeleti of rat at the level of which neither the messenger nor the protein are present. CFTR is detectable in the smooth muscle by immunoprecipitation and phosphorylation in vitro by the protein kinase A. The pharmacology of CFTR has been studied using iodide efflux in muscle cell freshly dissociated from rat aorta. It is demonstrated by the inventors that agonists of the cAMP route such as forskolin, IBMX, cpt-cAMP and the VIP neuropeptide activate iodide efflux the pharmacological signature of which is that of CFTR. Its inhibition profile is similar to that of epithelial CFTR (sensitivity to glibenclamide and DPC but not to Calixarene). In experiments on $Cftr^{+/+}$ rat and mouse tissues, physiological activation of CFTR by VIP and pharmacological activation by the compounds MPB-07 and MPB-91 leads to a relaxation of the pre-contracted aorta. In mice invalidated for the CFTR gene (=$Cftr^{-/-}$ mouse, B6 mouse; 129-$CFTR^{tm1Unc.}$ supplied by the CNRS CDTA breeding centre of Orleans), this effect is very considerably reduced. Moreover, a greater contraction is observed in the KO animals in response to the constricting agents. FIG. 9 shows these results.

These results demonstrate (1) that CFTR is expressed and functional in the smooth muscle, (2) that its pharmacological profile both for activation and for inhibition is very similar to that of epithelial CFTR, (3) that its absence in KO mouse leads to vascular tension disorders very similar to those encountered in hypertension, (4) that benzo[c]quinoliziniums represent a new family of anti-hypertensive compounds, thus opening up a new route of pharmacological research and potential treatment of diseases linked to hypertension. These results demonstrate moreover that a molecule which proves to be a CFTR activator can act as a vasorelaxant and potential bronchodilator.

ns: non-significant difference between the 2 values compared

*: significant difference between the 2 values compared, $p<0.05$

**: significant difference between the 2 values compared, $p<0.01$

Figure 1:
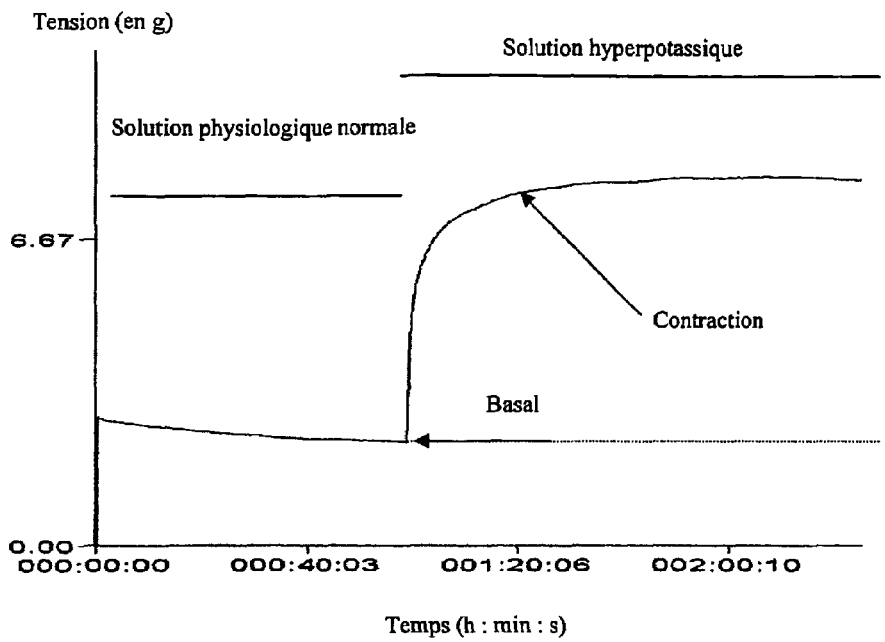
FIG. 1: A. Graph representing a contraction of aorta rings by a hyperpotassium solution
B. Graph representing a contraction of aorta rings by arterenol ($10^{-4}$ M)
Figure 1:
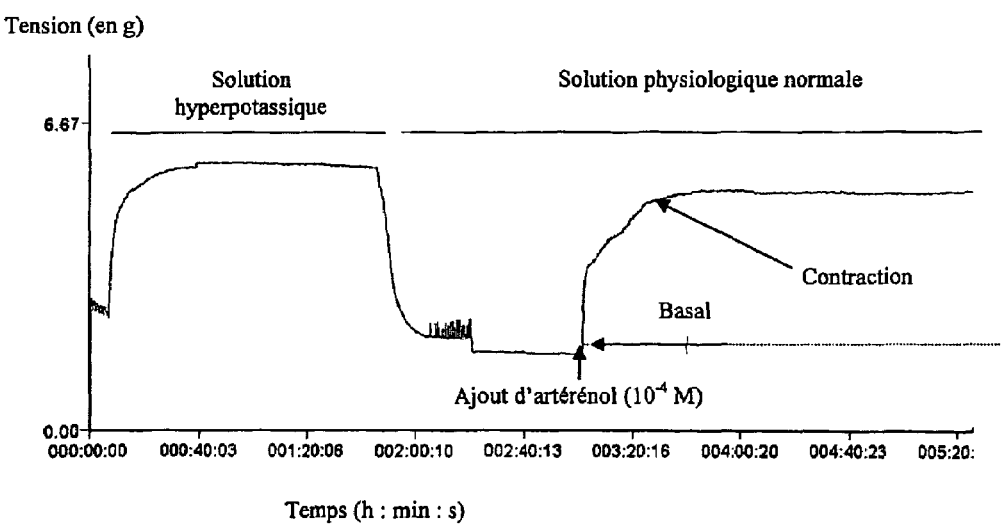
Figure 2:
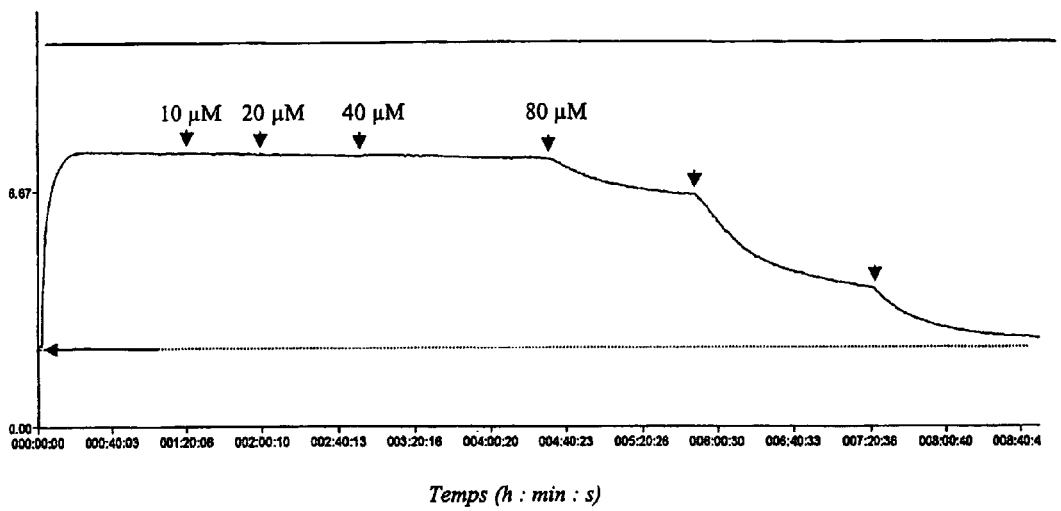
FIG. 2: Graphs representing a range of MPB-07: A. on aorta rings with endothelium pre-contracted in hyperpotassium solution; B. on aorta rings with endothelium pre-contracted in hyperpotassium solution, in the presence of L-NAME ($10^{-4}$M) in pre-incubation 30 minutes before the addition of MPB-07.
Figure 2:
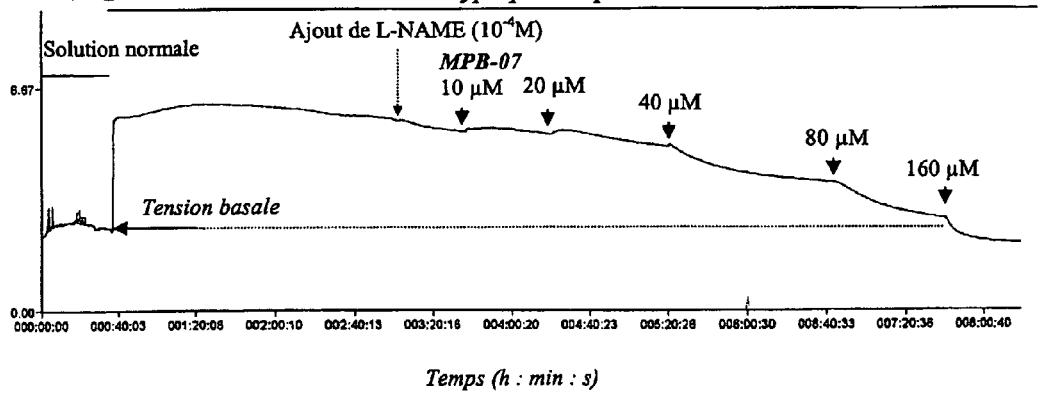
Figure 3:
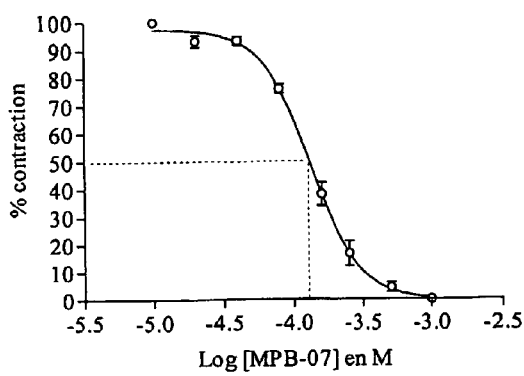
FIG. 3: Curves representing the percentage of contraction of the aorta rings as a function of the decimal logarithm of the MPB-07 concentration (in M). The range of MPB-07 (10, 20, 40, 80, 160, 250, 500 and 1000 µM) is tested on aorta rings pre-contracted in hyperpotassium solution (80 mM of KCl): A. with endothelium, average±SEM of n=14 experiments carried out on 4 rats; B. without endothelium, average±SEM of n=7 experiments carried out on 2 rats; C. with endothelium, in the presence of L-NAME ($10^{-4}$ M) in pre-incubation 30 minutes before the addition of MPB-07, average±SEM of n=8 experiments carried out on 2 rats; D. without endothelium, in the presence of L-NAME ($10^{-4}$ M) in pre-incubation 30 minutes before the addition of MPB-07, average±SEM of n=7 experiments carried out on 2 rats. The contraction percentage is calculated with respect to the value of maximum tension obtained in hyperpotassium solution. The results are standardized with respect to this value.
Figure 3:
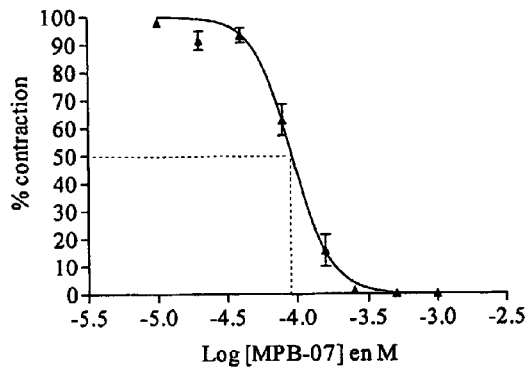
Figure 3:
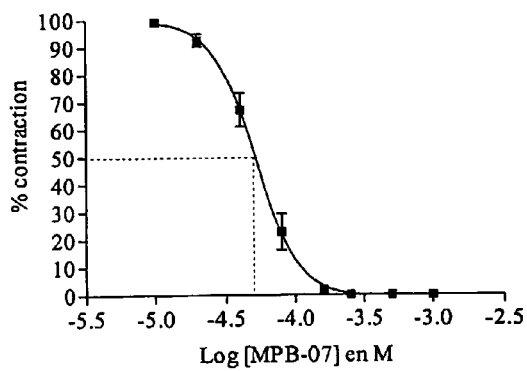
Figure 3:
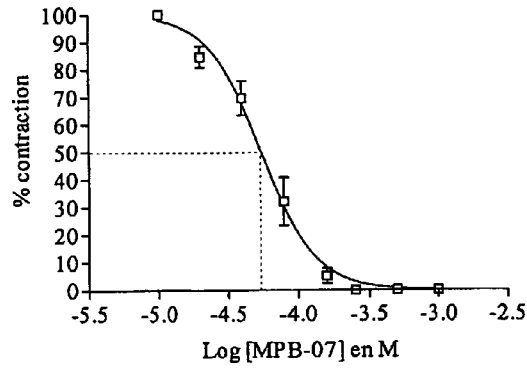
Figure 4:
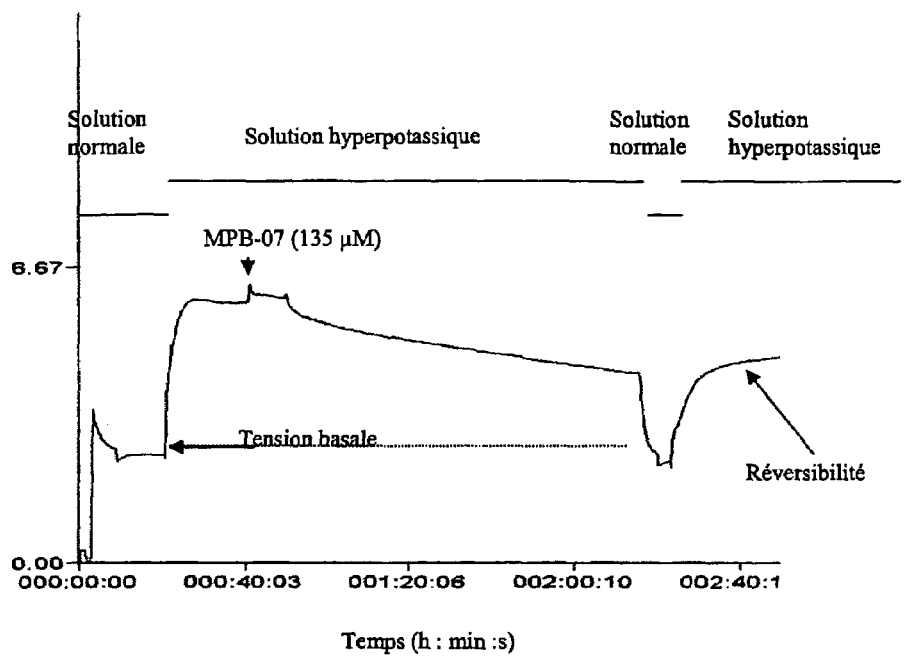
FIG. 4: A. Graph representing the reversibility of the effect of MPB-07 (135 µM) on aorta rings with endothelium B. Graph representing the effect of MPB-07 (10 µM) on aorta rings with endothelium pre-contracted by arterenol ($10^{-4}$ M).
Figure 4:
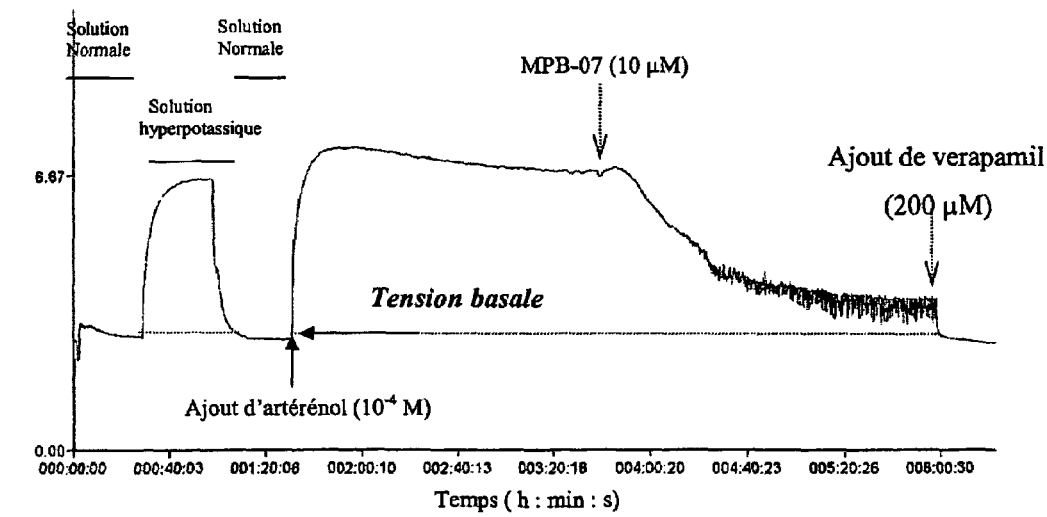
Figure 5:
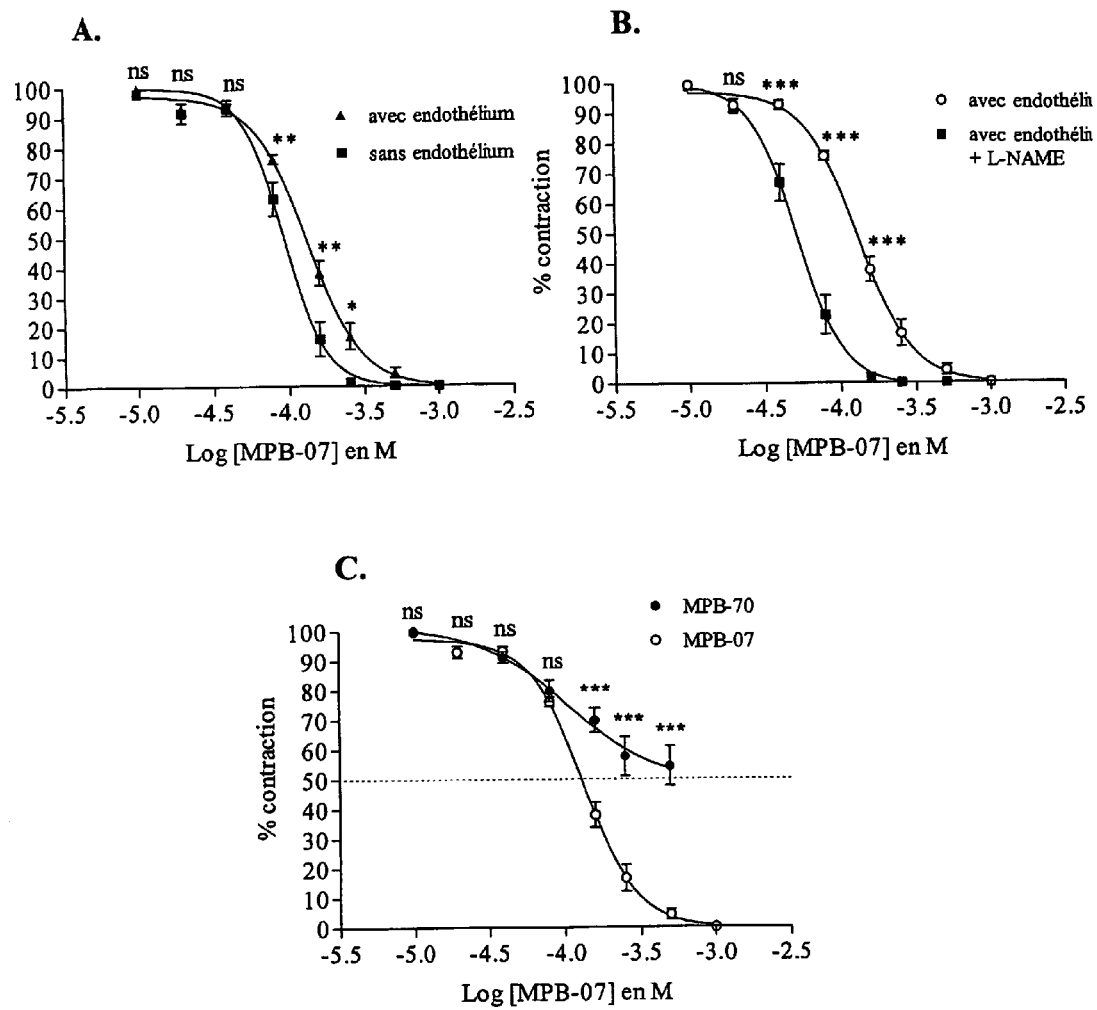
FIG. 5: Statistical comparison of the doses/responses of MPB-07 between aorta rings: A. with endothelium and without endothelium B. with endothelium and with endothelium in the presence of L-NAME ($10^{-4}$ M); C. Comparison of the doses/responses of MPB-07 and MPB-70 on aorta rings with endothelium. The results are presented as a contraction percentage as a function of the decimal logarithm of the MPB-07 concentration. The contraction values for each concentration are compared statistically, by Student's test.
Figure 6:
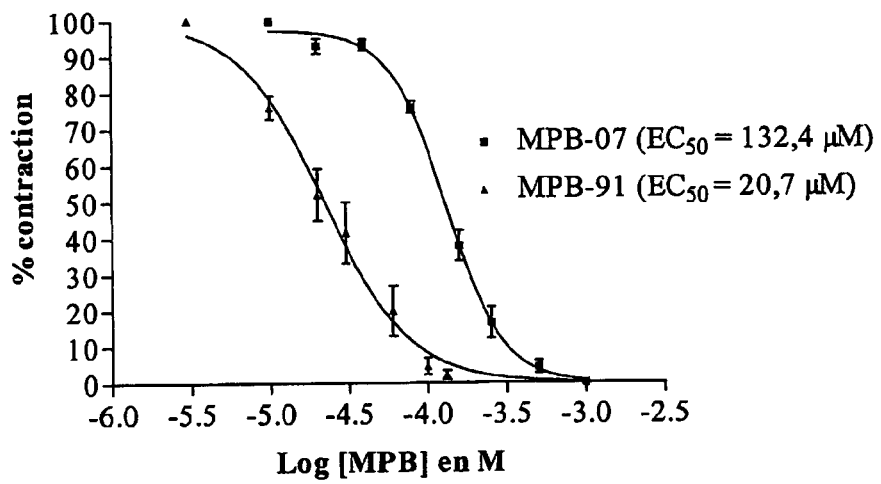

FIG. 6: Comparison of the dose/response curves of MPB-07 and MPB-91: The results are presented as a contraction percentage as a function of the decimal logarithm of the MPB-07 concentration.

Figure 7:
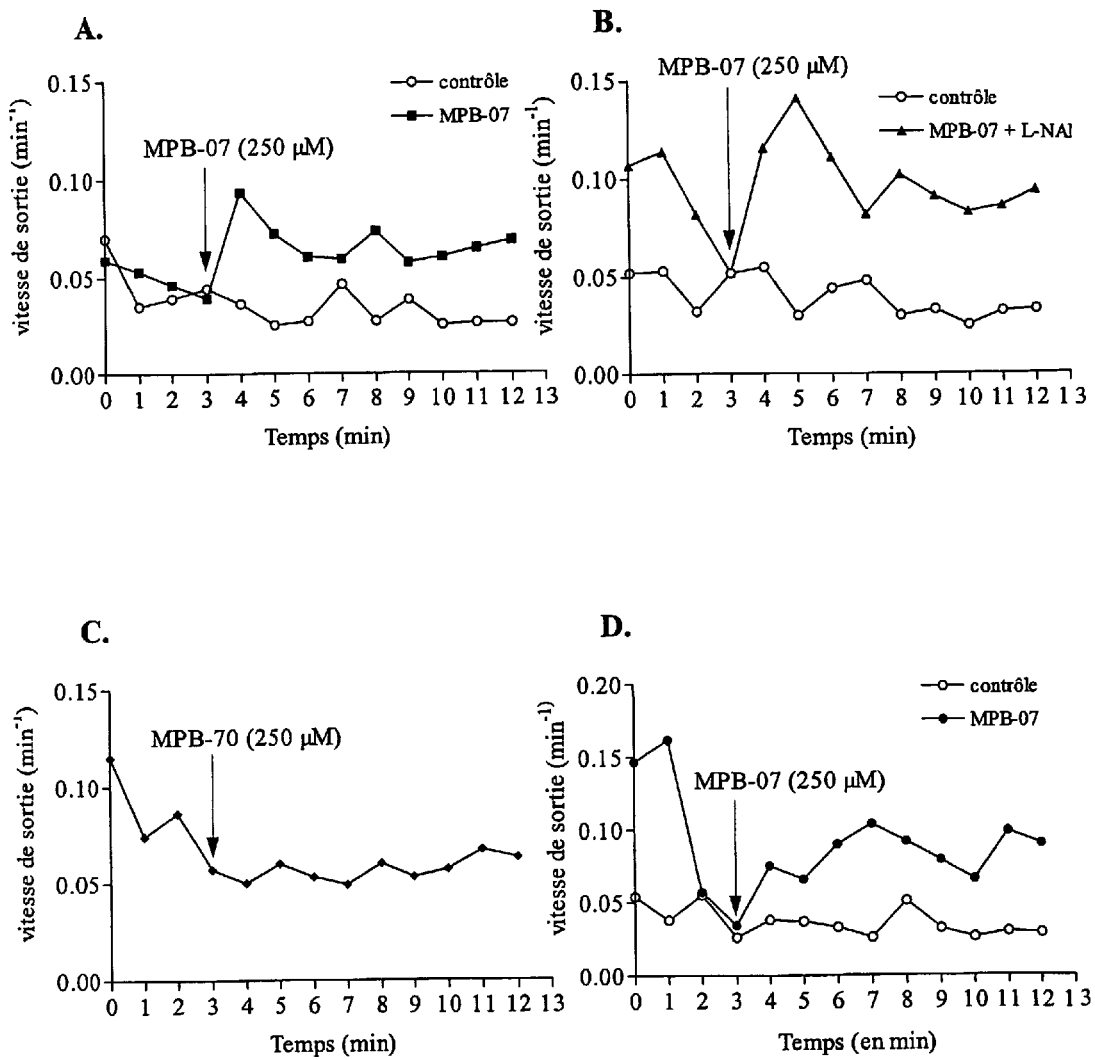

FIG. 7: Results representing iodide effluxes on aorta rings without endothelium: A. in the presence of MPB-07 (250 µM) in hyperpotassium medium; B. in the presence of MPB-07 (250 µM) in hyperpotassium medium and L-NAME ($10^{-4}$M) in pre-incubation 30 minutes before the addition of MPB-07; C. in the presence of MPB-70 (250 µM) in hyperpotassium medium; D. in the presence of MPB-07 (250 µM) in normal physiological medium.

The MPB-07 or MPB-70 is added after 4 minutes. The value at time 4 minutes is taken as the control value. The discharge speed is represented as a function of time.

Figure 8:
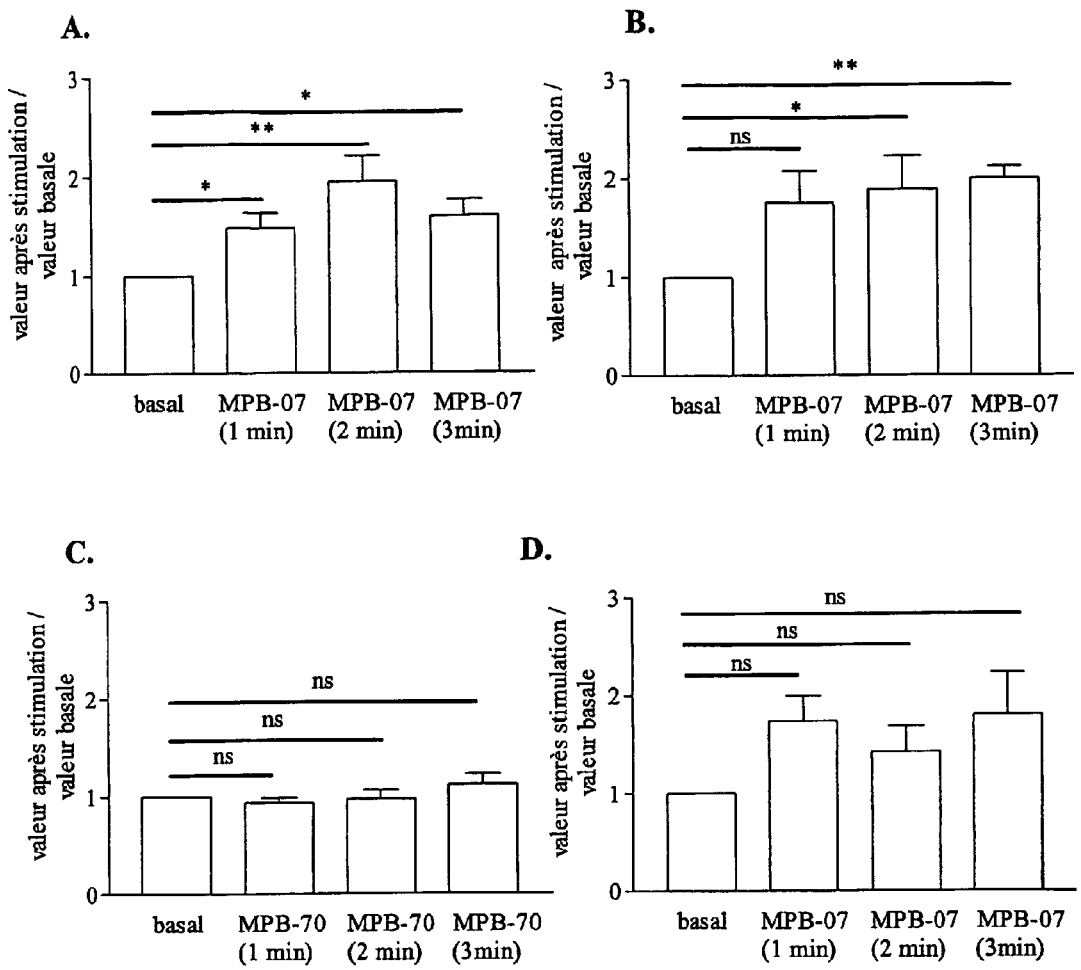

FIG. 8: Representation of the ratio of the discharge speed value obtained after different stimulation times and the discharge speed value before stimulation.

A. stimulation by MPB-07 in hyperpotassium medium, average±SEM of n=8 experiments; B. stimulation by MPB-07 in hyperpotassium medium, in the presence of L-NAME ($10^{-4}$ M) 30 minutes before the addition, average±SEM of n=4 experiments; C. stimulation by MPB-70, in hyperpotassium medium, average±SEM of n=4 experiments; D. stimulation by MPB-07 in normal physiological medium, average±SEM of n=3 experiments. The results are compared statistically (Student's t test) with respect to the basal value.

ns: difference non significant with respect to the basal value

*: difference significant with respect to the basal value, p<0.05

**: difference significant with respect to the basal value, p<0.01

Figure 9:
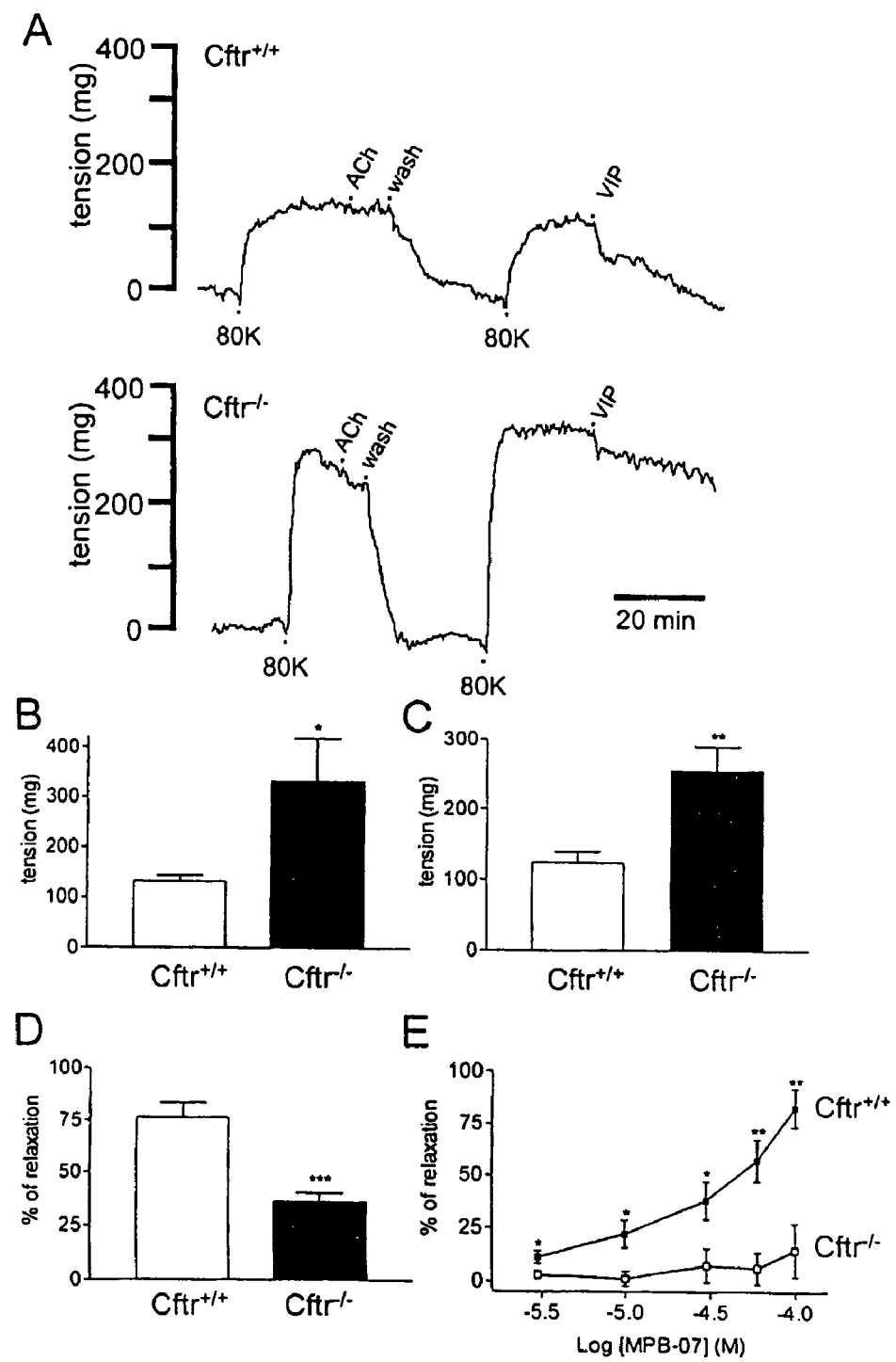

FIG. 9: Demonstration of the existence of an abnormal vascular tonus and altered vasorelaxation in a mouse invalidated for the CFTR gene (Cftr$^{-/-}$ mouse)

a, graphs showing the vasorelaxation induced by the VIP neuropeptide (Vasoactive Intestinal Polypeptide) of aortas without endothelium of Cftr$^{+/+}$ (left) and Cftr$^{-/-}$ (right) mice. The aorta rings are reversibly contracted by a hyperpotassium solution (solution of 80 mM K$^+$) then the effect of 300 nM VIP is measured. The absence of endothelium is verified by the addition of acetylcholine (ACh, $10^{-5}$ M).

b, Histograms of average tensions measured in response to a solution of 80 mM K$^+$ for Cftr$^{+/+}$ and Cftr$^{-/-}$ mice with (left) and without (right) endothelium.

C, Histograms of average vasorelaxation percentages induced by 300 nM VIP after constriction of the aorta rings by 80 mM K$^+$ for Cftr$^{+/+}$ and Cftr$^{-/-}$ mice.

d, Concentration-response curves for compound MPB-07 showing a vasorelaxation of aorta rings contracted by 80 mM K$^+$ in Cftr$^{+/+}$ mice (IC$_{50}$+37±1.17 µM, n=6). This effect is absent in Cftr$^{-/-}$ mice (n=6). Average±SEM*P<0.05,  P<0.01, * P<0.001.

BIBLIOGRAPHY

DORMER, R. L., DERAND, R., MCNEILLY, C. M., METTEY, Y., BULTEAU-PIGNOUX, L., METAYE, T., VIERFOND, J. M., GRAY, M. A., GALIETTA, L. J., MORRIS, M. R., PEREIRA, M. M., DOULL, I. J., BECQ, F. & MCPHERSON, M. A. (2001). Correction of delF508-CFTR activity with benzo(c)quinolizinium compounds through facilitation of its processing in cystic fibrosis airway cells. In *J Cell Sci. pp.* 4073-81.

BECQ, F., METTEY, Y., GRAY, M. A., GALIETTA, L. J., DORMER, R. L., MERTEN, M., METAYE, T., CHAPPE, V., MARVINGT-MOUNIR, C., ZEGARRA-MORAN, O., TARRAN, R., BULTEAU, L., DERAND, R., PEREIRA, M. M., MCPHERSON, M. A., ROGIER, C., JOFFRE, M., ARGENT, B. E., SARROUILHE, D., KAMMOUNI, W., FIGARELLA, C., VERRIER, B., GOLA, M. & VIERFOND, J. M. (1999). Development of substituted Benzo[c]quinolizinium compounds as novel activators of the cystic fibrosis chloride channel. *J Biol Chem,* 274, 27415-25.

DERAND, R., BULTEAU-PIGNOUX, L., METTEY, Y., ZEGARRA-MORAN, O., HOWELL, L. D., RANDAK, C., GALIETTA, L. J., COHN, J. A., NOREZ, C., ROMIO, L., VIERFOND, J. M., JOFFRE, M. & BECQ, F. (2001). Activation of G551D CFTR channel with MPB-91: regulation by ATPase activity and phosphorylation. *Am J Physiol Cell Physiol,* 281, C1657-66.

VENGLARIK, C. J., BRIDGES, R. J. & FRIZZELL, R. A. (1990). A simple assay for agonist-regulated Cl and K conductances in salt-secreting epithelial cells. *Am J Physiol,* 259, C358-64.

The invention claimed is:

1. A method for the treatment of a pathology associated with the constriction of smooth muscle cells selected from arterial hypertension and asthma in a subject in need thereof, said method comprising administering to said subject a compound of formula (Ia):

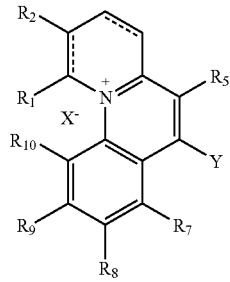

(Ia)

in which:
R$_1$ and R$_2$ represent a hydrogen atom,
R$_5$ represents a hydrogen atom, or a linear or substituted alkyl group with 1 to 10 carbon atoms, or an ester of formula COOR' in which R' represents a linear or substituted alkyl group with 1 to 10 carbon atoms,
Y represents an —OH, —SH, or —NH$_2$ group,
each of R$_7$, R$_8$, R$_9$, and R$_{10}$ is, independently, a hydrogen, chlorine, bromine, or fluorine atom, and
X represents an anion.

2. The method of claim 1, wherein said pathology is arterial hypertension.

3. The method of claim 1, wherein said pathology is asthma.

4. The method of claim 1, wherein X is chloride, bromide, or perchlorate.

5. The method of claim 1, wherein R$_5$ is a butyl group.

6. The method of claim 1, wherein R' is an ethyl group.

7. The method of claim 1, wherein said compound of formula (Ia) is selected from the following compounds:

compound 13 (MPB-01)

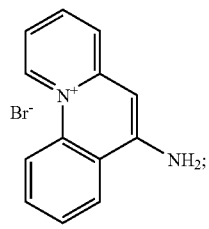

-continued
compound 11 (MPB-26)
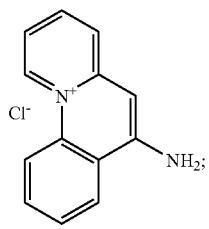
compound 14 (MPB-02)
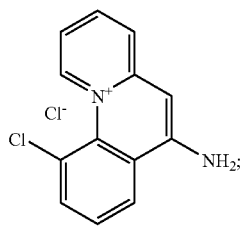
compound 15 (MPB-03)
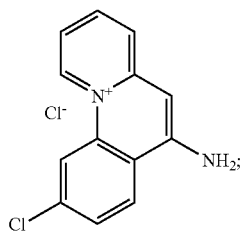
compound 16
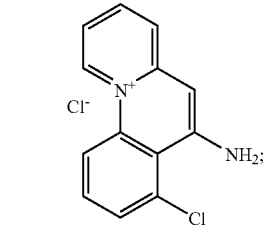
compound 17
compound 24
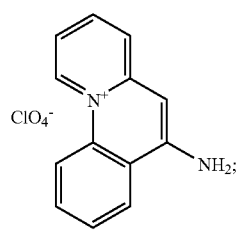
-continued
compound 12 (MPB-05)
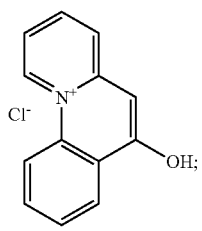
compound 18 (MPB-06)
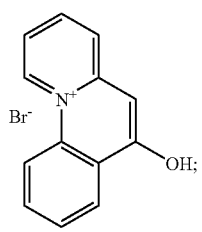
compound MPB 73
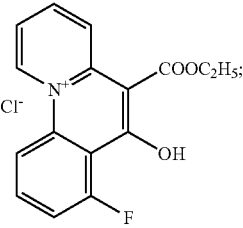
compound MPB 75
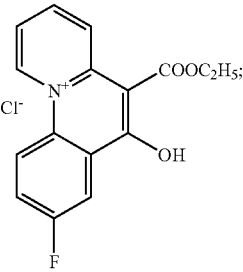
compound MPB 86
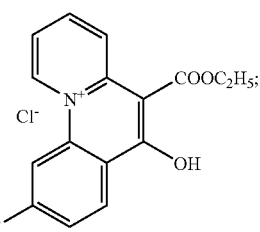
compound MPB 77
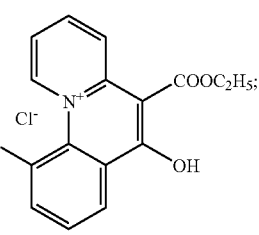

-continued
compound MPB 87
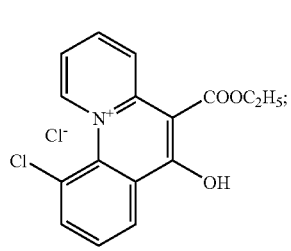
compound MPB 88
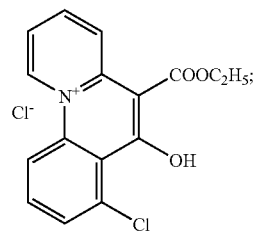
compound MPB 102
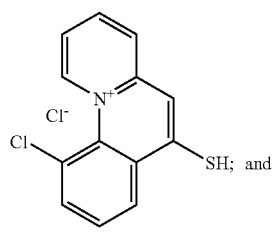
compound MPB 103
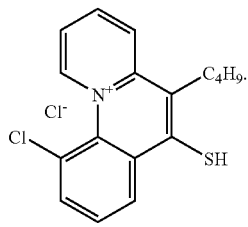
8. The method of claim 1, wherein said compound of formula (Ia) is MPB-07 of the following formula:
compound 19 (MPB-07)
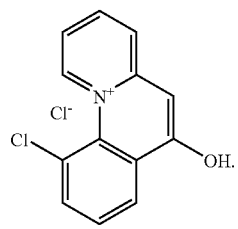
9. The method of claim 1, wherein said compound of formula (Ia) is MPB-91 of the following formula:
compound MPB-91
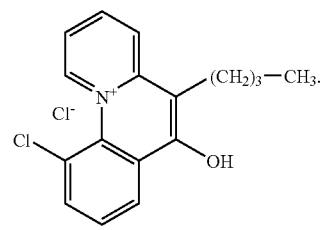
10. A compound selected from:
compound MPB 73
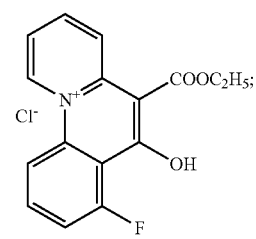
compound MPB 75
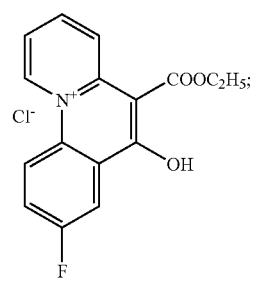
compound MPB 86
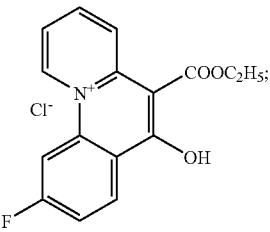
compound MPB 77
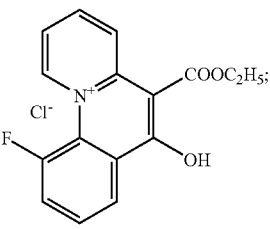
compound MPB 87
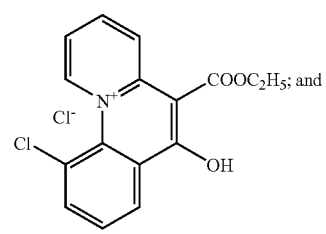

-continued
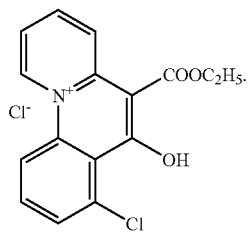
compound MPB 88
11. A compound selected from:
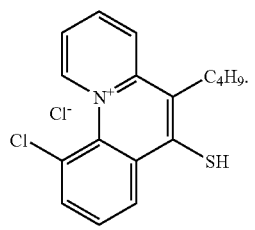
compound MPB 102
-continued
compound MPB 103
12. A pharmaceutical composition comprising a compound of claim 10 in combination with a pharmaceutically acceptable carrier.
13. A pharmaceutical composition comprising a compound of claim 11 in combination with a pharmaceutically acceptable carrier.
* * * * *

UNITED STATES PATENT AND TRADEMARK OFFICE
CERTIFICATE OF CORRECTION

PATENT NO. : 7,897,610 B2
APPLICATION NO. : 10/516839
DATED : March 1, 2011
INVENTOR(S) : Becq et al.

Page 1 of 2

It is certified that error appears in the above-identified patent and that said Letters Patent is hereby corrected as shown below:

Column 11, Line 8, replace "represents" with --represent a--.

Column 17, Line 13, replace "N.-nitro-L-arginine methyl ester" with --N·-nitro-L-arginine methyl ester--.

Column 26, Lines 15-34, replace

"compound 18 (MPB-06)

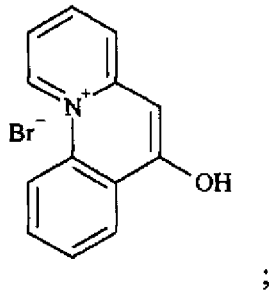

;

compound MPB 73

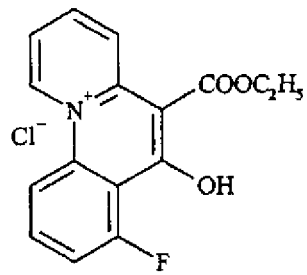

;"

with

--compound 18 (MPB-06)

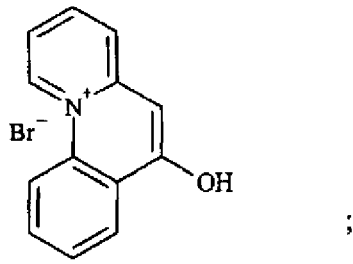

;

compound 19 (MPB-07)

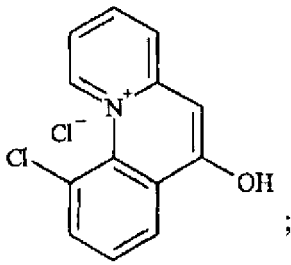

;

Signed and Sealed this
Twenty-fourth Day of April, 2012

David J. Kappos
*Director of the United States Patent and Trademark Office* compound 20 (MPB-08)
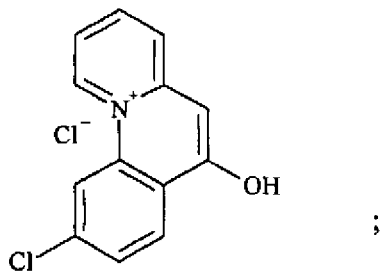
;
compound 21 (MPB-27)
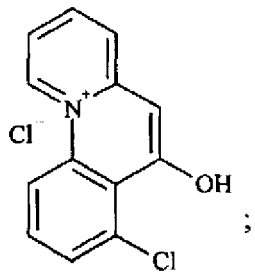
;
compound 25 (MPB-30)
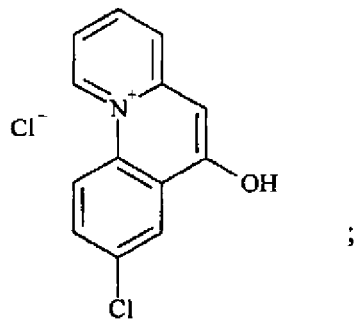
;
compound 26 (MPB-29)
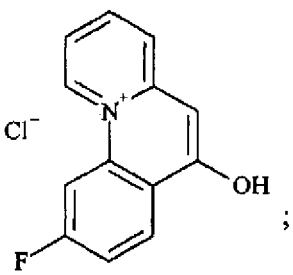
;
compound 27 (MPB-32)
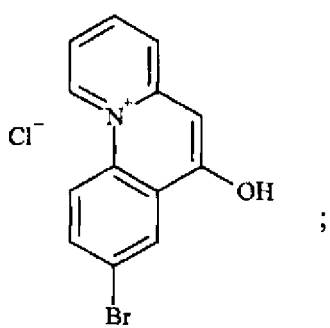
;
compound MPB-91
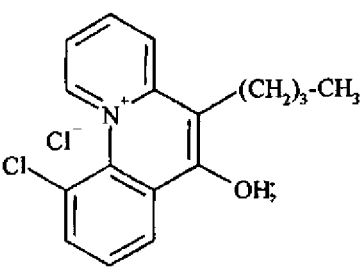
;
compound MPB 73
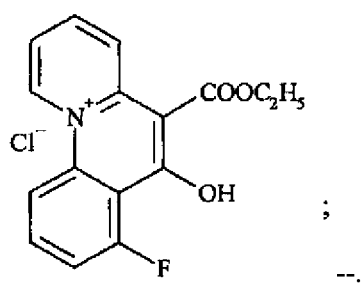
; --.